(12) United States Patent
Young

(10) Patent No.: US 7,169,113 B1
(45) Date of Patent: Jan. 30, 2007

(54) PORTRAYAL OF HUMAN INFORMATION VISUALIZATION

(75) Inventor: Charles E. Young, Albuquerque, NM (US)

(73) Assignee: Hello-Hello, Inc., Albuquerque, NM (US)

( * ) Notice: Subject to any disclaimer, the term of this patent is extended or adjusted under 35 U.S.C. 154(b) by 0 days.

(21) Appl. No.: 09/517,195

(22) Filed: Mar. 2, 2000

Related U.S. Application Data

(63) Continuation of application No. PCT/US98/18434, filed on Sep. 4, 1998.

(60) Provisional application No. 60/057,973, filed on Sep. 5, 1997.

(51) Int. Cl.
*A61B 13/00* (2006.01)

(52) U.S. Cl. .......................... 600/558; 705/1; 345/419; 345/422; 345/421; 345/473; 348/51; 348/42; 348/47; 348/589; 348/569; 348/468; 348/565; 359/23

(58) Field of Classification Search ................. 725/13, 725/22, 24, 32–36; 345/751, 716, 717, 719, 345/733, 419, 422, 421, 473, 42, 47, 51, 345/569, 589, 468, 565; 705/14, 10, 1; 600/558; 359/23

See application file for complete search history.

(56) References Cited

U.S. PATENT DOCUMENTS

| 4,646,145 A | | 2/1987 | Percy et al. ................... 358/84 |
|---|---|---|---|
| 4,789,235 A | * | 12/1988 | Borah et al. ................. 351/246 |
| 4,861,154 A | | 8/1989 | Sherwin et al. ............. 351/205 |
| 4,931,865 A | * | 6/1990 | Scarampi ...................... 725/12 |
| 5,052,401 A | | 10/1991 | Sherwin ...................... 128/745 |
| 5,220,501 A | * | 6/1993 | Lawlor et al. ................. 705/40 |
| 5,227,874 A | | 7/1993 | Von Kohorn ................. 358/84 |
| 5,331,969 A | | 7/1994 | Silberstein ................... 128/731 |
| 5,424,945 A | * | 6/1995 | Bell ............................... 705/1 |
| 5,465,729 A | | 11/1995 | Bittman et al. ............. 128/732 |
| 5,544,354 A | * | 8/1996 | May et al. ...................... 707/4 |
| 5,676,138 A | * | 10/1997 | Zawilinski ................... 600/301 |
| 5,731,805 A | * | 3/1998 | Tognazzini et al. ......... 345/156 |
| 6,118,427 A | * | 9/2000 | Buxton et al. .............. 345/629 |

OTHER PUBLICATIONS

Michael Crighton et al., Looker, 1981, The Ladd Co., wysiwyg://25/http://www.roogulator.esmartweb.com/sf/looker.*

Michael Crighton et al., Looker, 1981, The Ladd Co., ☐☐http://www.tvguide.com/Movies/database/showmovie.asp.*

* cited by examiner

*Primary Examiner*—James A Reagan
(74) *Attorney, Agent, or Firm*—Deborah A. Peacock; Philip D. Askenazy; Peacock Myers, P.C.

(57) ABSTRACT

An apparatus and method for displaying viewer reactions to a display object. The display object is divided into a plurality of spatial regions, viewer reactions are collected to an exposure to the display object and correlated with the spatial regions, and the display object is displayed with an aspect of the display of each spatial region being a function of the viewer reactions for the region.

33 Claims, 5 Drawing Sheets

½ Second

The consumer's eye is attracted to the message in the
boxes [with the words "my pet"] and
the dog at the top of the ad.

1 Second

The attention moves down from the store's logo
(to the boxes with the "PetSmart" logo].

Finally the consumer begins examining the prices of products featured on the sides [framing the center blocks].

PORTRAYAL OF HUMAN INFORMATION VISUALIZATION

CROSS-REFERENCE TO RELATED APPLICATIONS

This is a continuation of International Application PCT/US98/18434, with an international filing date of Sep. 4, 1998. This application also claims the benefit of the filing of U.S. Provisional Patent Application Ser. No. 60/057,973, entitled *Method for Displaying How Humans Visually Process Information*, filed on Sep. 5, 1997, and the specification thereof is incorporated herein by reference.

BACKGROUND OF THE INVENTION

1. Field of the Invention (Technical Field):

The present invention relates to display of information concerning human information visualization, particularly of two-dimensional objects such as advertisements.

2. Background Art

In developing effective means to communicate with people using visual presentations, means for determining effectiveness of such presentations are required. In order to create effective advertisements, for example, one must have an effective means of judging the effects of the advertisement on the consumer. Preferably, such means must be easily and intuitively understood by decision makers at all levels.

Prior mechanisms for assessing information concerning consumer processing of visual information, of varying complexity, include U.S. Pat. No. 5,676,138, to Zawilinski, entitled "Emotional Response Analyzer System with Multimedia Display"; U.S. Pat. No. 5,465,729, to Bittman et al., entitled "Method and Apparatus for Biofeedback"; U.S. Pat. No. 5,331,969, to Silberstein, entitled "Equipment for Testing or Measuring Brain Activity"; U.S. Pat. No. 5,227,874, to Von Kohorn, entitled "Method for Measuring the Effectiveness of Stimuli On Decisions of Shoppers"; U.S. Pat. No. 5,052,401, to Sherwin, entitled "Product Detector for a Steady Visual Evoked Potential Stimulator and Product Detector"; U.S. Pat. No. 4,861,154, to Sherwin et al., entitled "Automated Visual Assessment System With Steady State Visual Evoked Potential Stimulator and Product Detector"; and U.S. Pat. No. 4,647,964, to Weinblatt, entitled "Technique for Testing Television Commercials".

None of the above patents discloses the technique of the present invention in displaying information about reaction to an image by breaking the image into matrix cells and varying transparency of cells depending on information gathered about that cell. None of the prior disclosures are believed to have the intuitive impact of the present invention, and therefore are unlikely to be as successful in providing accurate information to decision makers.

SUMMARY OF THE INVENTION (DISCLOSURE OF THE INVENTION)

The present invention is of an apparatus and method for displaying viewer reactions to a display object comprising: dividing the display object into a plurality of spatial regions; collecting viewer reactions to an exposure to the display object; correlating the viewer reactions with the spatial regions; and displaying the display object with an aspect of the display of each spatial region being a function of the viewer reactions for the region. In the preferred embodiment, the display object is divided into a matrix, with each spatial region being a cell of the matrix. Collecting is preferably by exposing a viewer, or a plurality of viewers, to the display object for a duration between ¼ and 4 second, and most preferably a plurality of exposures to the display object are employed. The display object is displayed with the transparency (and/or color tingeing) of each spatial region being a function of the viewer reactions for the region. A static image (or images) may be displayed, or a motion picture sequence employed, preferably of a plurality of images corresponding to a plurality of viewer exposures to the display image.

A primary object of the present invention is to provide a straightforward means for displaying information collected about a display object's impact on viewers.

A primary advantage of the present invention is that it is intuitively understandable by decision makers at all levels.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The purpose of the present invention is to provide an intuitively appealing method for displaying diagnostic research data or information collected about how an audience or sample of research subjects processes and responds to visually complex display objects. Such a method aids decision makers in quickly seeing the strengths and weaknesses of different elements of a display object in terms of how well they elicit desired effects.

An "display object", for purposes of the specification and claims, is any visual stimulus represented or projected on a two-dimensional surface and designed to communicate a specific set of messages in order to elicit an intended response from viewers of that stimulus. Display objects include print advertisements, pages from catalogs, magazines or other printed publications, and screens from pages published electronically, as on the Internet or CD-ROMs. Display objects also include photographs or artistic renderings used as virtual representations of three dimensional communication spaces such as store environments, exhibition spaces, or street scenes (e.g., one cluttered with signage).

The present invention is designed to work with various manners of data collection that measure a human response to various parts of a display object. Two data collection methods are preferred, but others will be seen to be useful with the present invention by one skilled in the art.

The first preferred data collection approach makes use of controlled time exposures via a computerized interview. Each respondent is exposed to the display object on a computer screen for a sequence of measured time periods. For example, the respondent might be exposed to the test for three time exposures: ½ second, 1 second, and 4 seconds. After each exposure, the respondent is asked to record what he or she saw. The respondent may also be asked to indicate where exactly on the page or screen he or she saw items and that data is recorded on a grid. The information is then coded to determine how long it takes for viewers to register key elements such as a headline, a character, a package, a brand name, or the like. Depending on the purposes of the study, different time periods and a different number of exposures may be used. This method of data collection measures the order in which respondents take in or process the information contained in a display object.

The second preferred data collection approach is concerned with how people respond to the different parts of the display object. Response can refer to likeability or appeal, purchase interest, relevance, or some other measure of emotional or cognitive response. For this measurement, respondents are shown a copy of the display object with a grid or matrix superimposed over it and are asked to provide a rating of their level of response to each cell of the matrix.

Figure 1:
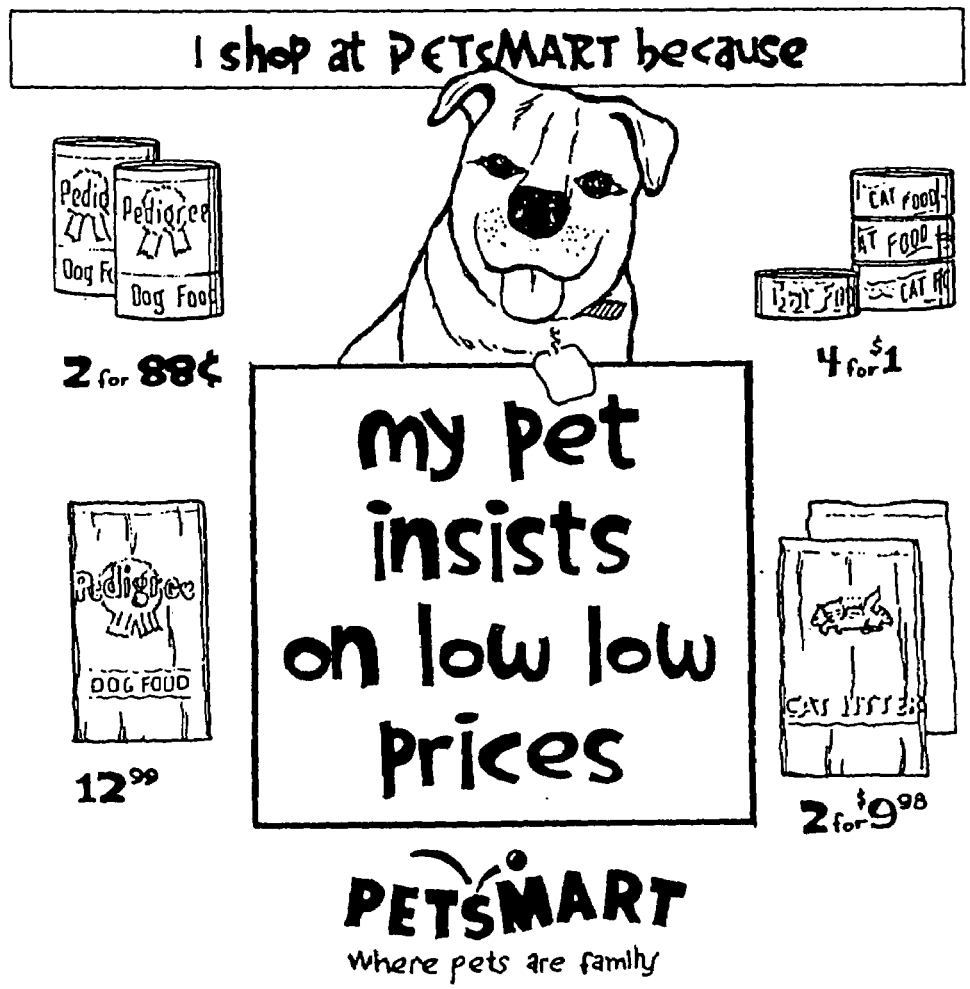
FIG. 1 illustrates a display object to be displayed according to the invention.

The invention is of a method of displaying information gathered about a display object, such as that of FIG. 1, divided into a grid. First, an opaque screen in the form of an n×m matrix is superimposed on a copy of the display object. Next, the research measurement associated with a particular cell of the matrix is used to determine the degree of transparency of the part of the screen covering that cell. For example, if after a ¼ second exposure, 30% of respondents indicated that they noticed a package in the part of the display object contained in cell 1×2, then the degree of transparency of the opaque screen covering cell 1×2 would be set to a value which is a function of 30%, such as the function x=x, which results in a 30% transparency. This adjustment is preferably performed for all cells in the matrix for each measurement taken.

Figure 2:
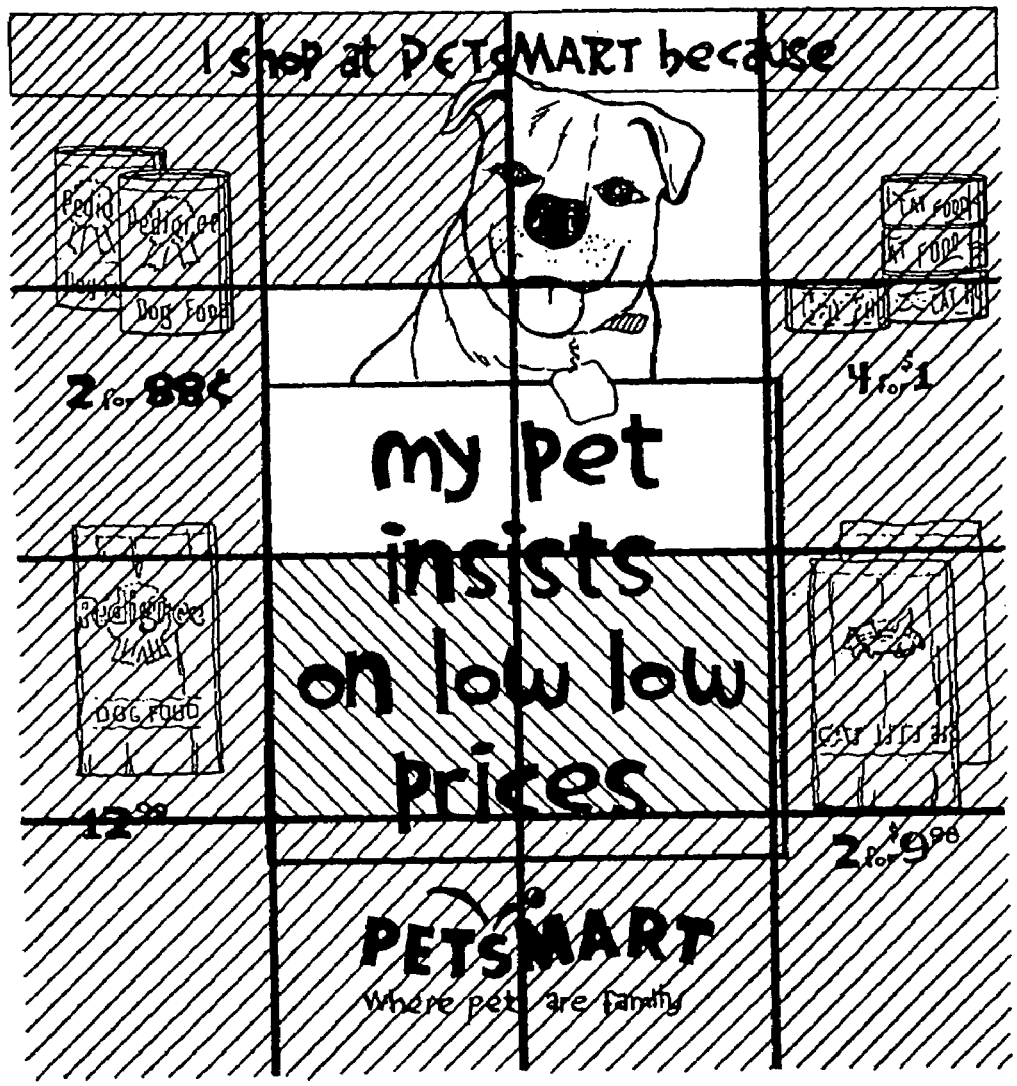
FIGS. 2–4 illustrate the display of the invention of viewer information collected about the display object of FIG. 1 at ½, 1, and 4 second exposures, respectively.
Figure 3:
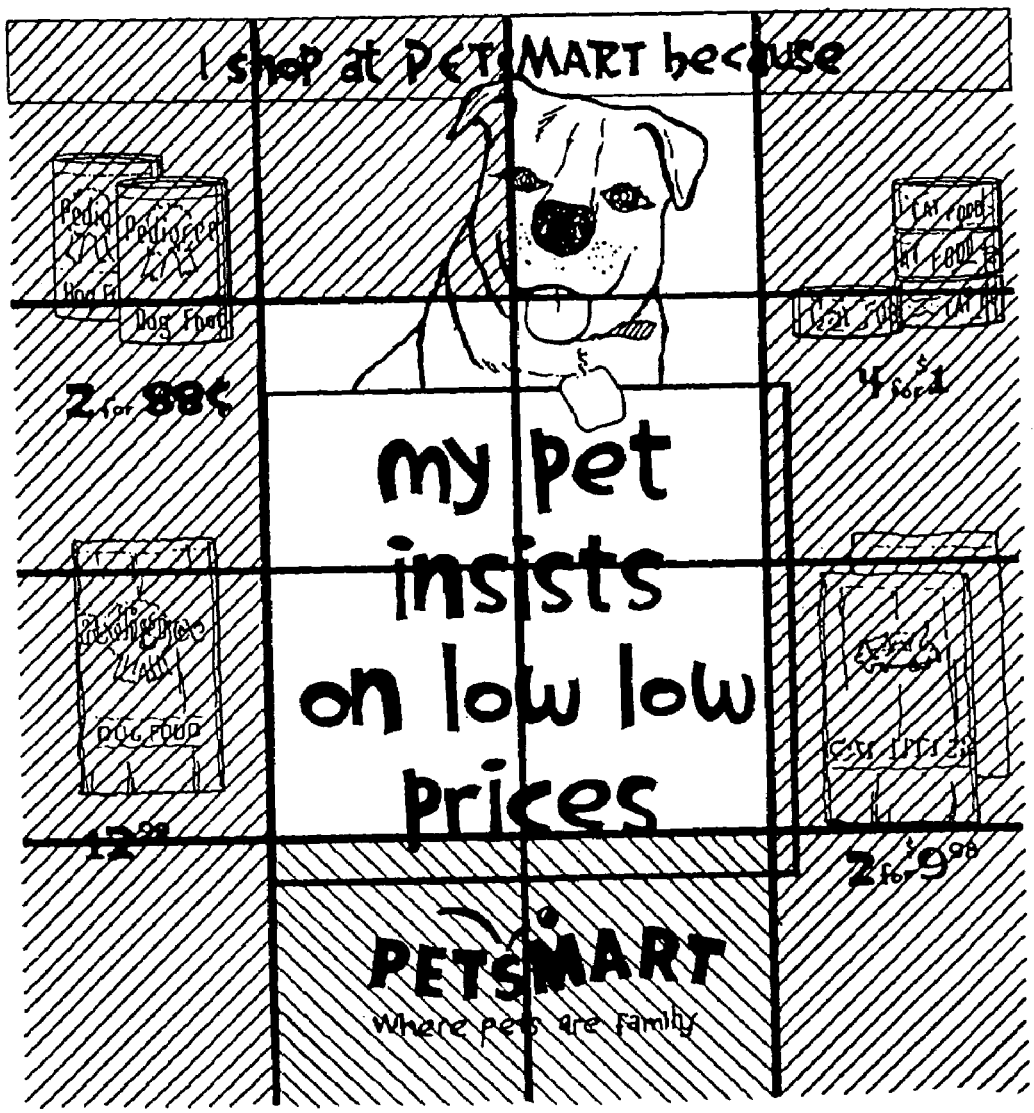
Figure 4:
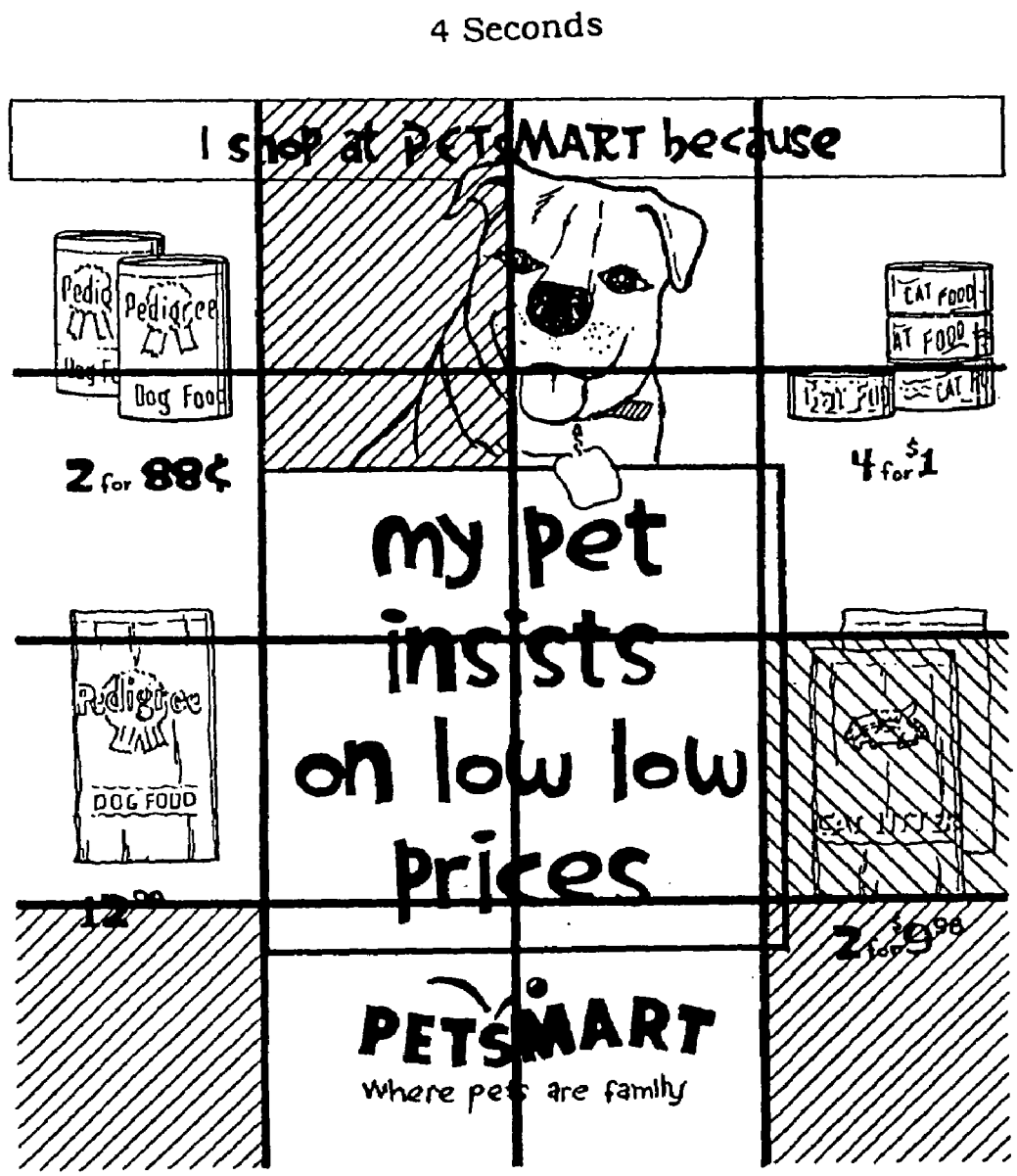

In order to display the sequence of viewer information processing, two types of display may be used. The first display presents all of the measurements collected simultaneously in a side-by-side arrangement of the different display screens associated with the timed exposures. An example of this type of display is shown in FIGS. 2–4. FIG. 2 shows that the consumer's eye at the ½ second mark is attracted to the message in the yellow box and the dog at the top of the display object. FIG. 3 shows that the attention at the 1-second mark moves down to the store's logo. FIG. 4 shows that at the 4-second mark the consumer begins examining the prices of products featured on the sides of the display object. A second display type is in the form of a movie that shows the progression of viewer attention in a more dynamic way, with a dramatic effect much like that of a photograph developing in the darkroom of viewer consciousness.

In order to display information about viewer response, a similar approach is used insofar as a semi-transparent screen divided into measurement cells is superimposed on the display object. In order to remind decision-makers that a different measurement is being referred to in the display, color may be used with the degree of color saturation indexed to the underlying measurement.

Figure 5:
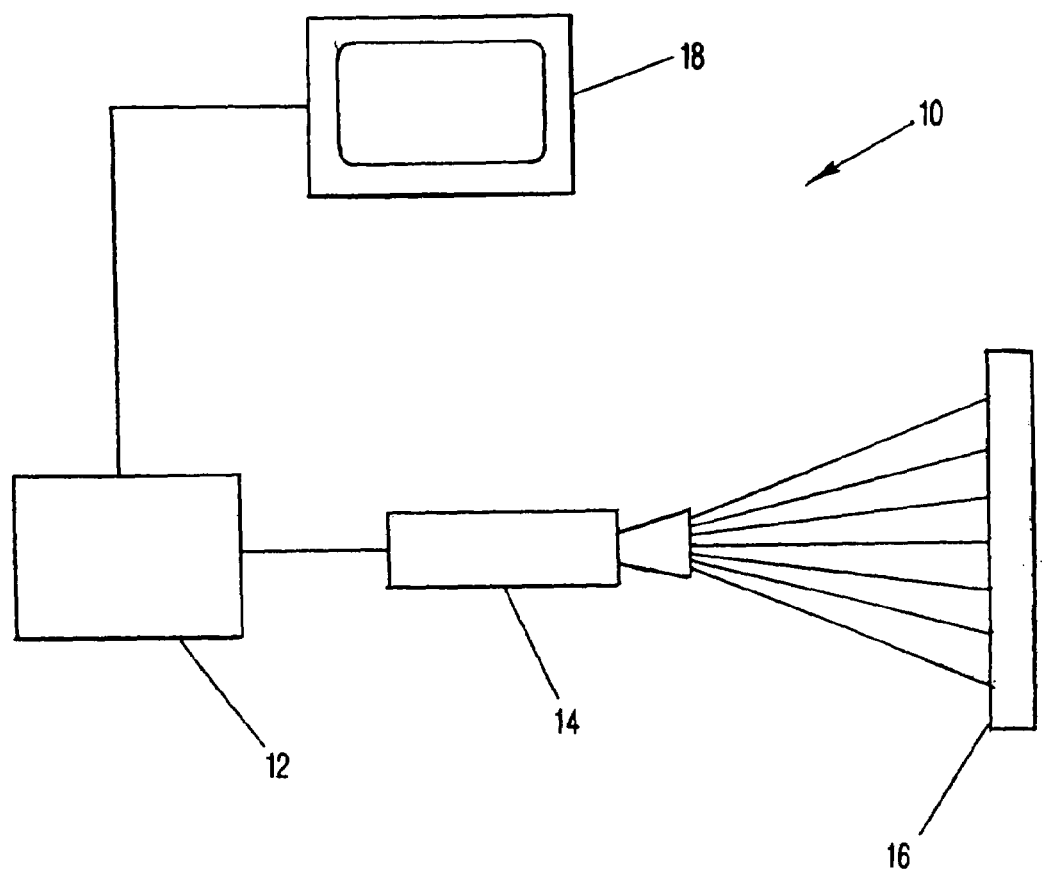
FIG. 5 is a schematic diagram of the preferred apparatus of the invention.

FIG. 5 illustrates the preferred embodiment of the apparatus of the invention 10. Personal computer 12, or like image processor, is used to receive and/or calculate the correlations between collected information from viewers and spatial regions of a display object designated by the user. The personal computer or image processor then places into video memory (or like storage) an appropriate image of the display object with spatial regions assigned different transparencies and/or color tingeing. Images according to the invention may then be displayed in any manner known to the art, such as on a display 18 or on surface 16 via projector 14 (such as a liquid-crystal device (LCD) projector).

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for displaying, collecting and evaluating viewer reactions to a display object comprising a plurality of elements, for the purposes of a decision maker's evaluation of the display object, the method comprising the steps of:

displaying an undivided display object on a display screen for a predetermined time of between approximately ¼ second and 4 seconds to at least one viewer for the purposes of collecting viewer reactions to the display object;

removing the undivided display object from view of the at least one viewer;

collecting cognitive viewer reactions to at least one element of the display object after the at least one viewer has viewed the undivided display object;

dividing the display object into a plurality of spatial regions, such spatial regions being mapped to the display object, after the step of displaying the display object to at least one viewer;

correlating the previously collected viewer reactions with the spatial regions of the display object;

image processing, using a computer or other processor, the previously collected viewer reactions corresponding to each spatial region;

displaying to the decision maker, and not the at least one viewer, the display object with at least one characteristic based on the viewer reactions corresponding to each spatial region.

2. The method of claim 1 wherein the viewer reactions comprise at least one cognitive response selected from the group consisting of memory of elements, likeability, appeal, purchase interest, relevance, and emotional response.

3. The method of claim 1 wherein the image processing step comprises correlating viewer responses with at least one characteristic selected from the group consisting of coloring, color saturation, transparency, superimposition, opacity and tingeing.

4. The method of claim 1 further comprising the step of the decision maker determining whether the display object elicited desired effects in the viewer, and strengths and weaknesses of each spatial region of the display object.

5. The method of claim 1 comprising:
displaying the object to the viewer for a first short predetermined time;
collecting first viewer reactions to the first short display;
displaying the object to the viewer for a second longer predetermined time; and
collecting second viewer reactions to the second longer display; and
displaying to the decision maker a plurality of images, wherein each image is derived from each of the collected viewer reactions.

6. The method of claim 1 wherein the displaying to the decision maker step comprises providing static images to the decision maker.

7. The method of claim 1 wherein the displaying to the decision maker step comprises playing a movie of the images to the decision maker.

8. The method of claim 1 wherein the step of displaying the display object on a display screen comprises displaying the display object on a computer screen.

9. The method of claim 1 wherein each spatial region comprises a cell of a matrix.

10. The method of claim 1 wherein the step of collecting cognitive viewer reactions comprises recording remembered elements.

11. The method of claim 1 further comprising the step of determining how long it takes the viewer to register the elements.

12. The method of claim 1 wherein the step of collecting cognitive viewer reactions comprises recording the location on the screen where the viewer remembered seeing the elements.

13. The method of claim 1 wherein the displaying to the decision maker step comprises displaying on a computer screen.

14. The method of claim 1 wherein the displaying to the decision maker step comprises displaying via a projector onto a surface.

15. The method of claim 1 wherein the at least one characteristic of a spatial region is determined by the percentage of viewers having reactions to one or more elements located in the spatial region.

16. The method of claim 1 wherein the display object comprises at least one object selected from the group consisting of a print advertisement, a page from a catalog, magazine, or other printed publication, an electronically published page, an internet page, a CD-ROM page, a photograph, an artistic rendering, and a visual representation.

17. The method of claim 1 wherein the at least one element comprises an object selected from the group consisting of a headline, a character, a figure, a word, a package, a brand, and a logo.

18. An apparatus for measuring viewer response to a display object comprising a plurality of elements, the apparatus comprising:
a display for displaying an undivided display object to one or more viewers for at least one predetermined time exposure comprising a duration of between approximately ¼ second and 4 seconds;
a data collector for receiving responses from the viewers regarding at least one of the elements after the viewers have viewed said display and the undivided display object has been removed from view of the one or more viewers;
a processor for correlating the responses to a plurality of spatial regions mapped to the display object and assigning at least one characteristic to each of said spatial regions based on the responses; and
a display for displaying the display object divided into said spatial regions having said at least one characteristic to one or more decision makers but not to the one or more viewers.

19. The apparatus of claim 18 wherein said display object comprises a visual stimulus represented or projected on a two-dimensional surface.

20. The apparatus of claim 18 wherein either of said displays comprises a computer screen.

21. The apparatus of claim 18 wherein said display for displaying the display object divided into said spatial regions comprises a projector.

22. The apparatus of claim 18 wherein said display of the display object comprises a visual stimulus designed to communicate a specific set of messages in order to elicit a response from viewers of the display object.

23. The apparatus of claim 18 wherein said display object comprises at least one object selected from the group consisting of a print advertisement, a page from a catalog, magazine, or other printed publication, an electronically published page, an internet page, a CD-ROM page, a photograph, an artistic rendering, and a visual representation.

24. The apparatus of claim 18 wherein said display for displaying an undivided display object displays said display object for a sequence of predetermined time exposures.

25. The apparatus of claim 18 wherein said processor determines a time length for viewers to register at least one element of the display object.

26. The apparatus of claim 18 wherein said at least one element comprises an object selected from the group consisting of a headline, a character, a figure, a word, a package, a brand, and a logo.

27. The apparatus of claim 18 wherein said data collector records viewer responses to different elements.

28. The apparatus of claim 18 wherein said viewer responses comprise at least one response selected from the group consisting of memory of elements, length of time for the view to register an element, location on the display where the viewer remembered seeing an element, likeability, appeal, purchase interest, relevance, an emotional response, and a cognitive response.

29. The apparatus of claim 18 wherein said characteristic is selected from the group consisting of coloring, color saturation, transparency, superimposition, opacity, and tingeing.

30. The apparatus of claim 18 wherein said at least one characteristic of a selected spatial region is determined by the percentage of viewers having at least one response to one or more elements located in said selected spatial region.

31. The apparatus of claim 18 wherein each said spatial region comprises a cell of a matrix.

32. The apparatus of claim 18 wherein said display for displaying the display object divided into said spatial regions comprises one or more images displayed statically.

33. The apparatus of claim 18 wherein said display for displaying the display object divided into said spatial regions comprises a movie.

* * * * *